United States Patent
Sudo et al.

(10) Patent No.: US 9,074,264 B2
(45) Date of Patent: Jul. 7, 2015

(54) METHOD FOR RECOVERING PRECIOUS METAL FROM SOLUTION CONTAINING PRECIOUS METAL IONS, EXTRACTING AGENT OR ADSORBENT USED THEREFOR, AND BACK-EXTRACTING AGENT OR DESORBENT

(75) Inventors: Yukinori Sudo, Shunan (JP); Takashi Sakaki, Shunan (JP)

(73) Assignee: TOSOH CORPORATION, Yamaguchi (JP)

( * ) Notice: Subject to any disclaimer, the term of this patent is extended or adjusted under 35 U.S.C. 154(b) by 142 days.

(21) Appl. No.: 13/976,591

(22) PCT Filed: Dec. 28, 2011

(86) PCT No.: PCT/JP2011/080479
§ 371 (c)(1),
(2), (4) Date: Jun. 27, 2013

(87) PCT Pub. No.: WO2012/091125
PCT Pub. Date: Jul. 5, 2012

(65) Prior Publication Data
US 2013/0281726 A1    Oct. 24, 2013

(30) Foreign Application Priority Data

Dec. 28, 2010 (JP) ................... 2010-292588
Feb. 23, 2011 (JP) ................... 2011-037052

(51) Int. Cl.
| C22B 3/00 | (2006.01) |
| C25C 1/00 | (2006.01) |
| C22B 3/26 | (2006.01) |
| C22B 3/24 | (2006.01) |
| B01J 20/32 | (2006.01) |
| B01J 38/48 | (2006.01) |
| B01J 23/96 | (2006.01) |
| C07C 323/60 | (2006.01) |
| C07D 285/00 | (2006.01) |
| C25C 1/20 | (2006.01) |

(52) U.S. Cl.
CPC ............. *C22B 11/04* (2013.01); *C22B 3/0005* (2013.01); *C22B 3/24* (2013.01); *B01J 20/3204* (2013.01); *B01J 20/3251* (2013.01); *B01J 38/48* (2013.01); *B01J 23/96* (2013.01); *C25C 1/00* (2013.01); *C07C 323/60* (2013.01); *C07D 285/00* (2013.01); *C25C 1/20* (2013.01)

(58) Field of Classification Search
CPC .... B01J 38/48; B01J 20/3204; B01J 20/3251; B01J 23/96; C07C 1/20; C07C 323/60; C22B 3/0005; C22B 3/24; C22B 11/04; C07D 285/00
See application file for complete search history.

(56) References Cited

U.S. PATENT DOCUMENTS

| 2,910,373 | A | 10/1959 | Chenicek |
| 4,279,805 | A | 7/1981 | Ohzeki et al. |
| 2007/0172404 | A1 | 7/2007 | Narita et al. |
| 2009/0178513 | A1 | 7/2009 | Narita et al. |

FOREIGN PATENT DOCUMENTS

| JP | 44-31464 | 12/1969 |
| JP | 55-94944 | 7/1980 |
| JP | 4-363345 | 12/1992 |
| JP | 5-105973 | 4/1993 |
| JP | 9-279264 | 10/1997 |
| JP | 2010-59533 | 5/2010 |
| JP | 2011-41916 | 3/2011 |
| JP | 2011-41918 | 3/2011 |
| WO | WO 2005/083131 | 9/2005 |
| WO | WO 2011/021696 | 2/2011 |

OTHER PUBLICATIONS

CN Office Action in CN201180062457.X dated Aug. 5, 2014.
Pan et al, "Dibutyl Sulfide: Synthesis, Pd, Pt Extraction and Separation Studies", Chinese Journal of Inorganic Chemistry, vol. 24, No. 4, pp. 520-526, 2008.
English translation of CN Office Action in CN201180062457.X dated Aug. 5, 2014.
International Search Report for PCT/JP2011/080479, mailed Mar. 27, 2012.

*Primary Examiner* — Porfirio Nazario Gonzalez
(74) *Attorney, Agent, or Firm* — Nixon & Vanderhye P.C.

(57) ABSTRACT

To provide a method for recovering a precious metal from a solution containing precious metal ions, an extracting agent or adsorbent used therefor, and a back-extracting agent or desorbent.
An extracting agent or adsorbent in which precious metal ions are extracted or adsorbed, is brought into contact with a back-extracting agent or desorbent containing a sulfur-containing amino acid derivative represented by the following formula (I):

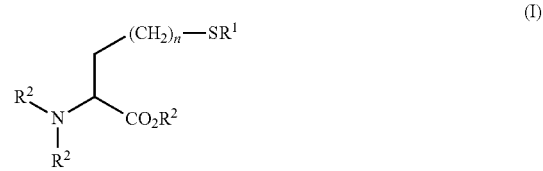

wherein $R^1$ is a methyl group, an ethyl group, a vinyl group, a $C_{3-8}$ linear, branched or cyclic hydrocarbon group, or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 0 or 1, to obtain a solution containing the precious metal ions, which is subjected to a reduction treatment to obtain a precious metal.

15 Claims, No Drawings

METHOD FOR RECOVERING PRECIOUS METAL FROM SOLUTION CONTAINING PRECIOUS METAL IONS, EXTRACTING AGENT OR ADSORBENT USED THEREFOR, AND BACK-EXTRACTING AGENT OR DESORBENT

TECHNICAL FIELD

This application is the U.S. national phase of International Application No. PCT/JP2011/080479 filed 28 Dec. 2011 which designated the U.S. and claims priority to Japanese Patent Application Nos. 2010-292588, filed Dec. 28, 2010 and 2011-037052, filed Feb. 23, 2011, the entire contents of each of which are hereby incorporated by reference.

The present invention relates to a method for recovering a precious metal, which comprises subjecting a solution containing precious metal ions obtained by extraction or adsorption by an extracting agent or an adsorbent and then back extraction or desorption, to a reduction treatment, an extracting agent or an adsorbent to be used therefor, and a back-extracting agent or a desorbent.

BACKGROUND ART

For industrial catalysts, automobile exhaust gas purifying catalysts and many electric appliances, precious metals such as palladium, platinum and rhodium have been used. Since precious metals are expensive and useful as resources, they have been recovered after use and recycled. In recent years, demands for the resources conservation are increasing, and importance of separation and recovery, and recycle of precious metals is more increasing.

To separate and recover a precious metal, many methods such as a sedimentation separation method, an ion exchange method, an electrodeposition method and a solvent extraction method have been developed, and among them, a solvent extraction method has been widely employed in view of the economical efficiency and operation properties.

A solvent extraction method is one of methods to separate and recovery a precious metal. Specifically, it comprises an extracting step of subjecting an aqueous phase in which palladium ions are dissolved and an organic phase in which an oil-soluble extracting agent is dissolved to liquid-liquid contact to extract the palladium ions into the organic phase side, and a back extraction step of back-extracting the palladium ions which had been extracted to the organic phase side into the aqueous phase side again using an aqueous phase in which a back-extracting agent is dissolved. For example, extraction of palladium ions is carried out with an organic phase using a dialkyl sulfide compound as the extracting agent, and back extraction of palladium ions is carried out with an aqueous phase using an aqueous ammonia solution as the back-extracting agent (for example, Patent Document 1).

Further, in order to improve the extraction rate in the solvent extraction method, an extracting agent having an amide group introduced to the vicinity of sulfur in the dialkyl sulfide has been proposed, and a method for back-extracting palladium using an acidic thiourea aqueous solution as the back-extracting agent has been proposed (for example, Patent Document 2).

However, the above-described solvent extraction method has problems in view of the safety and the environmental burden, since a large quantity of an organic solvent is used.

Accordingly, as a method using no organic solvent, a method of adsorbing palladium ions has been proposed (for example, Patent document 3). In this method, as a ligand (receptor) of palladium ions, a specific sulfide compound is fixed on a styrene derivative polymer (for example, polychloromethylstyrene) carrier to prepare an insoluble palladium ion adsorbent, and this adsorbent is directly added to an aqueous solution in which palladium ions are dissolved to carry out adsorption of the palladium ions.

Further, the applicant has already been filed a patent application relating to an adsorbent comprising a compound having an amide group introduced to the vicinity of sulfur in a dialkyl sulfide as a ligand (for example, Patent Documents 4 and 5).

In a case where an extracting agent having an amide group introduced to the vicinity of sulfur in a dialkyl sulfide or an adsorbent comprising a compound having an amide group introduced to the vicinity of sulfur in a dialkyl sulfide as a ligand, is used, the back extraction rate or the desorption rate of palladium ions tends to be low if hydrochloric acid or ammonia is used as a back-extracting agent or desorbent, and accordingly usually a thiourea aqueous solution is preferably used (for example, Patent Document 5).

PRIOR ART DOCUMENTS

Patent Documents

Patent Document 1: JP-A-9-279264
Patent Document 2: WO2005/083131
Patent Document 3: JP-A-5-105973
Patent Document 4: JP-A-2011-41916
Patent Document 5: JP-A-2011-41918

DISCLOSURE OF INVENTION

Technical Problem

The present inventors have attempted to adsorb palladium ions in an aqueous solution using an adsorbent having a compound having an amide group introduced to the vicinity of sulfur in a dialkyl sulfide fixed on an alumina carrier, and then to desorb the adsorbed palladium ions. Further, they have used an acidic thiourea aqueous solution as a desorbent, whereupon a recovered liquid having the palladium ions quantitatively desorbed was obtained.

However, they have attempted electrolytic reduction of the recovered liquid so as to obtain metal palladium from the recovered liquid, whereupon the obtained metal palladium had low purity containing a large quantity of sulfur-containing impurities. It was found that a complicated high purification treatment is required to obtain high purity metal palladium from the low purity product.

On the other hand, in a case where the precious metal to be recovered is palladium, a precious metal ion extracting agent or adsorbent is required to have high separation properties from ions of precious metals other than palladium, such as platinum ions, in some cases. Specifically, there are high demands for separation and recovery of palladium from e.g. automobile exhaust gas purifying catalysts containing a large quantity of platinum relative to palladium, and jewelry, and a palladium ion extracting agent or adsorbent which highly selectively extract or adsorb palladium ions from a palladium ion-containing aqueous solution containing platinum ions has been required.

However, with a conventional palladium ion extracting agent or adsorbent, mutual separation of palladium ions and platinum ions with high selectivity is difficult.

Under these circumstances, the object of the present invention is to provide a method for recovering a precious metal, by which a high purity precious metal can be obtained, by efficiently back-extracting or desorbing precious metal ions obtained by extracting or adsorbing precious metal ions particularly palladium ions contained in a solution, and subjecting the obtained solution containing the precious metal ions to a reduction treatment.

Further, another object of the present invention is to provide a method for recovering a precious metal, by which a high purity palladium metal can be obtained, by selectively extracting or adsorbing palladium ions from a solution in which platinum group metal ions coexist, effectively back-extracting or desorbing the extracted or adsorbed palladium ions, and subjecting the obtained solution containing palladium ions to a reduction treatment.

Still another object of the present invention is to provide a back-extracting agent or desorbent capable of efficiently back-extracting or desorbing extracted or adsorbed precious metal ions particularly palladium ions to be used for the above method, and an extracting agent or adsorbent capable of selectively extracting or adsorbing palladium ions from a solution in which platinum group metal ions coexist.

Solution to Problem

The present inventors have conducted extensive studies to accomplish the above objects and as a result, they have found that a sulfur-containing amino acid derivative represented by the formula (I) has excellent back extraction property and desorption property for precious metal ions as compared with conventional hydrochloric acid, ammonia, thiourea or the like. Further, unexpectedly, they have found that a very high purity precious metal can easily be obtained by subjecting a recovered liquid obtained by back extraction or desorption using such a sulfur-containing amino acid derivative to a reduction treatment, as compared with a case of using conventional thiourea as a back-extracting agent or a desorbent, and accomplished the present invention.

Further, the present inventors have found that by using an amide-containing sulfide compound represented by the formula (II), palladium ions can selectively be extracted or adsorbed from a solution containing palladium ions in which platinum ions coexist. They have further found that high purity palladium can easily be recovered by subjecting a recovered solution obtained by back extraction or desorption by the sulfur-containing amino acid derivative represented by the above formula (I) from the extracting agent or adsorbent containing palladium ions thus obtained, and accomplished the present invention.

That is, the present invention provides the following.
1. A method for recovering a precious metal, which comprises bringing an extracting agent or adsorbent in which precious metal ions are extracted or adsorbed, into contact with a back-extracting agent or desorbent containing a sulfur-containing amino acid derivative represented by the following formula (I):

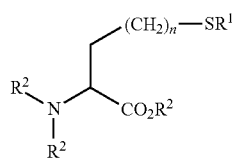

wherein $R^1$ is a methyl group, an ethyl group, a vinyl group, a $C_{3-8}$ linear, branched or cyclic hydrocarbon group, or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 0 or 1, to obtain a solution containing the precious metal ions, and subjecting the solution to a reduction treatment to obtain a precious metal.

2. A method for recovering a precious metal, which comprises bringing an adsorbent in which precious metal ions are adsorbed, into contact with a desorbent containing a sulfur-containing amino acid derivative represented by the above formula (I), to obtain a solution containing the precious metal ions, and subjecting the solution to a reduction treatment to obtain a precious metal.

3. The method for recovering a precious metal according to the above 1 or 2, wherein the precious metal ions are palladium ions, and the precious metal is palladium.

4. The method for recovering a precious metal according to any one of the above 1 to 3, wherein the sulfur-containing amino acid derivative is a compound of the formula (I) wherein $R^1$ is a methyl group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 1.

5. The method for recovering a precious metal according to any one of the above 1 to 3, wherein the sulfur-containing amino acid derivative is methionine.

6. The method for recovering a precious metal according to any one of the above 1 to 5, wherein the extracting agent or adsorbent contains an amide-containing sulfide compound represented by the formula (II):

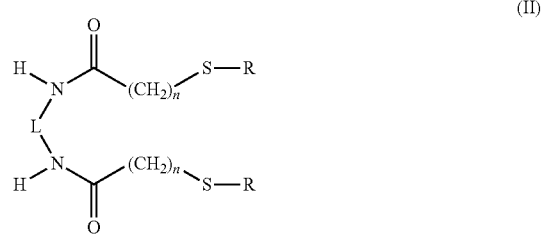

wherein R's are each independently a methyl group, an ethyl group, a $C_{3-18}$ chain hydrocarbon group, a $C_{3-10}$ alicyclic hydrocarbon group or a $C_{6-14}$ aromatic hydrocarbon group, n's are each independently an integer of from 1 to 4, and L is a methylene group, an ethylene group, a $C_{3-8}$ linear, branched or cyclic alkylene group, or a $C_{6-14}$ arylene group.

7. The method for recovering a precious metal according to the above 6, wherein the amide-containing sulfide compound is a compound of the formula (II) wherein R is n-octyl, and n is 1.

8. The method for recovering a precious metal according to any one of the above 1 to 7, wherein the adsorbent is fixed on a carrier.

9. The method for recovering a precious metal according to the above 8, wherein the carrier is alumina or silica gel.

10. The method for recovering a precious metal according to any one of the above 1 to 9, wherein the reduction treatment is electrolytic reduction by electrolysis.

11. A back-extracting agent or desorbent, which contains a sulfur-containing amino acid derivative represented by the above formula (I).

12. A desorbent, which contains a sulfur-containing amino acid derivative represented by the above formula (I).

13. An amide-containing sulfide compound represented by the above formula (II).
14. An extracting agent or adsorbent containing the amide-containing sulfide compound as defined in the above 13.
15. The adsorbent according to the above 14, wherein the amide-containing sulfide compound is fixed on a carrier.
16. The adsorbent according to the above 15, wherein the carrier is alumina or silica gel.

Advantageous Effects of Invention

According to the present invention, by using a sulfur-containing amino acid derivative represented by the formula (I), extracted or adsorbed precious metal ions particularly palladium ions can efficiently be back-extracted or desorbed, and further, by subjecting the obtainable recovered liquid containing precious metal ions particularly palladium ions to a reduction treatment, a high purity precious metal particularly metal palladium with a low content of impurities such as sulfur, which can hardly be obtained, can easily be obtained.

Further, in the present invention, in a case where the amide-containing sulfide compound represented by the formula (II) is used, palladium ions can highly selectively be extracted or adsorbed from a solution containing palladium ions in which platinum ions and the like coexist, and by subjecting a recovered liquid containing palladium obtained by back-extracting or desorbing the extracted or adsorbed palladium ions to a reduction treatment, high purity metal palladium with a low content of impurities such as sulfur can easily be obtained.

DESCRIPTION OF EMBODIMENTS (Back-Extracting Agent or Desorbent)

In the present invention, in the sulfur-containing amino acid derivative represented by the above formula (I) to be used for back extraction for desorption of extracted or adsorbed precious metal ions particularly palladium ions, $R^1$ is a methyl group, an ethyl group, a vinyl group, a $C_{3-8}$, preferably $C_{3-6}$ linear, branched or cyclic hydrocarbon group, or a $C_{6-14}$, preferably $C_{6-10}$ aromatic hydrocarbon group. A plurality of $R^2$'s in the formula (I) are each independently a hydrogen atom, a methyl group, an ethyl group, a vinyl group, a $C_{3-8}$, preferably $C_{3-6}$ linear, branched or cyclic hydrocarbon group, or a $C_{6-14}$, preferably $C_{6-10}$ aromatic hydrocarbon group, and n is 0 or 1.

The $C_{3-8}$ linear, branched or cyclic hydrocarbon group may, for example, be a propyl group, a butyl group, a pentyl group, a hexyl group, a heptyl group, an octyl group, an isopropyl group, an isobutyl group, a sec-butyl group, a tert-butyl group, an isopentyl group, a neopentyl group, a tert-pentyl group, a 2-ethylhexyl group, an allyl group, a 1-propenyl group, an isopropenyl group, a 1-butenyl group, a 2-butenyl group, a 2-methylallyl group, a 1-heptynyl group, a 1-hexenyl group, a 1-heptenyl group, a 1-octenyl group, a 2-methyl-1-propenyl group, a cyclopropyl group, a cyclobutyl group, a cyclopentyl group, a cyclohexyl group, a cyclohenptyl group, a cyclooctyl group, a cyclohexenyl group, a cyclohexadienyl group, a cyclohexatrienyl group, a cyclooctenyl group or a cyclooctadienyl group.

The $C_{6-14}$ aromatic hydrocarbon group may, for example, be a phenyl group, a naphthyl group, an anthryl group, a tolyl group, a xylyl group, a cumenyl group, a benzyl group, a phenethyl group, a styryl group, a cinnamyl group, a biphenyl group or a phenanthryl group.

Among them, in view of the precious metal ion back extraction property or desorption property, $R^1$ is preferably a methyl group or an ethyl group, and $R^2$'s are each independently preferably a hydrogen atom, a methyl group or an ethyl group. Particularly, in view of the precious metal ion back extraction property or desorption property and availability, particularly preferred is methionine wherein $R^1$ is a methyl group, all $R^2$'s are hydrogen atoms and n=1.

In the case of methionine among the sulfur-containing amino acid derivatives represented by the formula (I), the production example is shown below.

Methyl mercaptan and acrolein are reacted to produce 3-methyl mercaptopropione aldehyde, which is formed into a cyanohydrin by hydrocyanic acid to produce 3-methyl mercaptopropionic cyanhydrin. The obtained 3-methyl mercaptopropionic cyanhydrin is formed into hydantoin by carbon dioxide and ammonia to obtain M-hydantoin.

The obtained M-hydantoin is hydrolyzed in the presence of an alkali such as an alkali metal hydroxide such as sodium hydroxide or potassium hydroxide; an alkali metal carbonate such as sodium carbonate or potassium carbonate; or an alkali metal hydrogen carbonate such as sodium hydrogen carbonate or potassium hydrogen carbonate, to obtain an alkali metal salt of methionine. To the obtained alkali metal salt of methionine, sulfuric acid, hydrochloric acid, carbon dioxide or the like is added for neutralization thereby to crystallize methionine. The crystallized methionine can be collected by filtration, separation, washing with water as the case requires, and drying (for example, JP-A-2000-143617).

In the case of a methionine derivative wherein $R^1$ is a methyl group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n=1, among the sulfur-containing amino acid derivatives represented by the formula (I), the production example is shown below.

That is, methionine is formed into a N-alkyl (for example, Jikken Kagaku Koza (Experimental Chemistry), the fourth series, vol. 20, section 285), or into a N-aryl (for example, Tetrahedron Letters, 1998, vol. 39, page 2367) and/or into an ester (for example, Jikken Kagaku Koza (Experimental Chemistry), the fifth series, vol. 16, section 285) by using a known reagent to produce the methionine derivative represented by the formula (I).

In the case of a sulfur-containing amino acid derivative wherein $R^1$ is a methyl group, an ethyl group, a vinyl group, a $C_{3-8}$ linear, branched or cyclic hydrocarbon group or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n=1, among the sulfur-containing amino acid derivatives represented by the formula (I), the production example is shown below.

That is, by using, instead of the methyl mercaptan in the production process disclosed in JP-A-2000-143617, a compound of the following formula (22):

$$R^1\text{—SH} \quad (22)$$

(wherein $R^1$ is the same as $R^1$ in the formula (I)), S-substituted-2-amino-4-mercaptobutyric acid is obtained. The obtained S-substituted-2-amino-4-mercaptobutyric acid is formed into a N-alkyl (for example, the above document) or into a N-aryl (for example, the above document) and/or into an ester (for example, the above document), whereby a methionine derivative represented by the formula (I) wherein n=1 may optionally be produced.

In the case of a sulfur-containing amino acid derivative wherein $R^1$ is a methyl group, an ethyl group, a vinyl group, a $C_{3-8}$ linear, branched or cyclic hydrocarbon group or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n=0 among the sulfur-containing amino acid derivatives represented by the formula (I), the production example is shown below.

That is, cysteine is formed into an S-alkyl (for example, Shin Jikken Kagaku Koza (New Experimental Chemistry), vol. 16, section 1716), into an N-alkyl (for example, the above document) or into an N-aryl (for example, the above document) and/or into an ester (for example, the above document), whereby a sulfur-containing amino acid derivative represented by the formula (I) wherein n=0 may optionally be produced.

The sulfur-containing amino acid derivative represented by the formula (I) has an asymmetric center, and it may be any one of an S-form, an R-form and a racemic mixture. Further, the sulfur-containing amino acid derivative is not particularly limited, and may, for example, be a salt such as a hydrochloride, a nitrate, a sulfate, a lithium salt, a sodium salt, a potassium salt or a cesium salt.

(Back Extraction or Desorption Method by Back-Extracting Agent or Desorbent)

The sulfur-containing amino acid derivative represented by the formula (I) is used as a back-extracting agent or desorbent, and it is brought into contact with an extracting agent or adsorbent containing a precious metal obtained by being brought into contact with a solution containing precious metal ions, thereby to back-extract or desorb the precious metal ions.

The back-extracting agent or desorbent of the sulfur-containing amino acid derivative represented by the formula (I) is preferably in the form of an aqueous solution of the sulfur-containing amino acid derivative, and the concentration of the sulfur-containing amino acid derivative in the aqueous solution is not particularly limited and is usually preferably from 0.1 to 20 wt %. In the aqueous solution of the back-extracting agent or the desorbent, a salt such as sodium chloride, an organic solvent such as methanol, a polymer such as a polysaccharide or other third component may be dissolved.

The precious metal ion back-extracting agent or desorbent containing the sulfur-containing amino acid derivative represented by the formula (I) may be used under any of basic, neutral and acidic conditions, and it is preferably used under acidic conditions, for a reason such that an acidic aqueous solution is used in a process of extracting and in a process of adsorbing precious metal ions.

The acid to be used to make the back-extracting agent or the desorbent an acidic aqueous solution is not particularly limited, and is preferably an inorganic acid such as hydrochloric acid, sulfuric acid or nitric acid, particularly preferably hydrochloric acid. The acid concentration of the acidic aqueous solution is not particularly limited, and is preferably from 0.01 to 10 mol/L, more preferably from 0.1 to 5 mol/L. Particularly when the acid concentration is from 1 to 3 mol/L, precious metal ions can quantitatively be back-extracted or desorbed, and chemical damages of the extracting agent or adsorbent and elimination of precious metal ion ligands from the adsorbent can sufficiently be reduced to such an extent that the extracting agent or the adsorbent can be repeatedly used.

In the present invention, the precious metal ions to be back-extracted or desorbed using the back-extracting agent or desorbent containing the sulfur-containing amino acid derivative may be particularly precious metal ions having high affinity to a sulfur atom, such as palladium ions, platinum ions, gold ions, rhodium ions, iridium ions, ruthenium ions and osmium ions. Among them, palladium ions are preferred, and the palladium ions may coexist with the above precious metal ions.

In the back extraction or desorption using the sulfur-containing amino acid derivative, the amount of use of the back-extracting agent or the desorbent is not particularly limited, however, it is preferably adjusted so that the amount of the sulfur-containing amino acid derivative is 2 molar times of more, more preferably from 5 to 1,000 molar times, to 1 mol of the precious metal ions to be back-extracted or desorbed.

Further, back extraction or desorption is usually carried out under normal pressure or under atmospheric pressure, but may be carried out under elevated pressure or reduced pressure or in the presence of an inert gas. The precious metal ion back extraction or desorption is carried out usually in a temperature range of from 4 to 150° C., and is more preferably within a temperature range of from 10 to 50° C.

For the back extraction or desorption, another back-extracting agent or desorbent other than the sulfur-containing amino acid derivative represented by the formula (I) may be used in combination within a range not to impair the objects of the present invention.

By the above-described back extraction or desorption, a solution containing the sulfur-containing amino acid derivative represented by the formula (I) and the precious metal ions can be obtained.

(Recovery of Precious Metal by Reduction Treatment)

The solution containing precious metal ions back-extracted or desorbed by the back-extracting agent or desorbent containing the sulfur-containing amino acid derivative represented by the formula (I) (hereinafter sometimes referred to as solution for reduction treatment) is, as it is or after neutralized, subjected to a reduction treatment, whereby a precious metal can be obtained.

The solution for reduction treatment is preferably an aqueous solution. Further, in the aqueous solution, a salt such as sodium chloride, an organic solvent such as methanol, a polymer such as a polysaccharide or another third component may be dissolved.

The reduction treatment can be carried out under any conditions of acidic conditions, neutral conditions and basic conditions, however, preferably in neutral conditions with a pH of at least 6 and at most 8, in view of the reduction efficiency of precious metal ions and with a view to suppressing corrosion of facilities. In a case where the solution to be subjected to a reduction treatment is acidic, the neutralizing agent is not particularly limited and is preferably an inorganic base compound such as sodium hydroxide, potassium hydroxide, sodium bicarbonate or calcium hydroxide.

The concentration of the sulfur-containing amino acid derivative represented by the formula (I) contained in the solution for reduction treatment is not particularly limited, and is preferably at least 0.01 wt % and at most 30 wt %. Within this range, in view of economical efficiency, it is more preferably at least 0.01 wt % and at most 15 wt %.

The concentration of the precious metal ions in the solution for reduction treatment is not particularly limited, and is preferably at least 0.01 wt % and at most 20 wt %. Within this range, in view of economical efficiency, it is more preferably at least 0.01 wt % and at most 15 wt %. In a case where platinum group metal ions coexist, it is preferably at most 15 wt %, particularly preferably at most 10 wt %.

The reduction treatment is not particularly limited, and various methods may be employed depending upon the purpose and facilities. For example, an electrolytic reduction method by electrolysis, or a chemical reduction method of adding a reducing agent such as hydrogen gas or a boron hydride compound may be mentioned. Among them, an electrolytic reduction method by electrolysis is preferred in view of the operation efficiency and the cost.

The reduction treatment is carried out usually under normal pressure, particularly in an atmospheric pressure, but may be carried out under elevated pressure or reduced pressure or in an inert gas atmosphere. Further, the reduction treatment is carried out usually within a temperature range of from 4 to 100° C., more preferably within a temperature range of from 10 to 50° C.

In a case where the reduction treatment is carried out by an electrolytic reduction method, for example, a known electrolytic reduction treatment as disclosed in "Denki Kagaku Hanno Sosa to Denkaiso Kogaku (Electrochemical reaction processes and electrolytic cell engineering)", first edition, published by Kagaku-Dojin Publishing Company, INC, 1979, page 175 may be employed. For example, a titanium electrode covered with platinum may, for example, be used as an anode, and a titanium electrode, a copper electrode or a nickel electrode may, for example, be used as a cathode. Further, the electric current density is preferably from 0.001 to 100 $A/dm^2$, particularly preferably from 1 to 50 $A/dm^2$.

By the reduction treatment, a noble metal can be obtained, and the precious metal is obtained as a precious metal precipitate. The precious metal precipitate can be separated from the back-extracting agent or desorbent, water and the like by filtration. The filtration method may, for example, be a method using a membrane filter, filter paper, filter cloth, a glass filter or the like, and filtration by a membrane filter or filter paper is preferred in view of the operation efficiency. In such a manner, the precious metal can be produced and isolated from a recovered solution obtainable by the back extraction or desorption.

(Extraction or Adsorption of Precious Metal Ions from Solution Containing Precious Metal Ions)

In the present invention, in the back extraction or desorption of precious metal ions using the back-extracting agent or desorbent containing the sulfur-containing amino acid derivative represented by the formula (I), the extracting agent or adsorbent of precious metal ions to be treated is not particularly limited, and various agents may be mentioned. For example, an extracting agent comprising dihexyl sulfide or dioctyl sulfide may be mentioned.

Further, the adsorbent may, for example, be commercially available products such as SiliaBond series manufactured by SILICYCLE or QuadraPure series manufactured by Reaxa, or one having a known ligand to scavenge precious metal ions supported on a proper insoluble carrier. The ligand to scavenge precious metal ions is not particularly limited and is preferably a compound having a sulfide group or an amino group.

The extracting agent is used usually as dissolved in an organic solvent. The organic solvent is preferably one which is not miscible with water and is not particularly limited, and may, for example, be benzene, toluene, xylene, hexane, methylene chloride or chloroform.

Into the extracting agent, upon contact with an aqueous solution in which precious metal ions are dissolved, the precious metal ions are extracted. Then, the extracting agent separated from the aqueous solution in which the precious metal ions are dissolved, is brought into contact with the back-extracting agent containing the sulfur-containing amino acid derivative represented by the formula (I), whereupon the precious metal ions are desorbed from the extracting agent and back-extracted into a phase of the precious metal ion back-extracting agent. The contact and the mutual separation of the extracting agent and the back-extracting agent are not particularly limited, and for example, a separatory funnel may be used. A liquid/liquid separation apparatus having the same function as a separatory funnel may be used.

On the other hand, in the adsorbent having a ligand to scavenge precious metal ions supported on a proper insoluble carrier, the carrier on which the ligand to scavenge precious metal ions is fixed is not particularly limited so long as it is insoluble in water. It may, for example, be a synthetic high molecular weight carrier such as a styrene type polymer such as polystyrene or crosslinked polystyrene, a polyolefin such as polyethylene or polypropylene, a poly (halogenated olefin) such as polyvinyl chloride or polytetrafluoroethylene, a nitrile type polymer such as polyacrylonitrile, or a (meth) acrylate polymer such as polymethyl methacrylate or polyethyl methacrylate, a natural high molecular weight carrier such as cellulose, agarose or dextran, or an inorganic carrier such as activated carbon, silica gel, diatomaceous earth, hydroxyapatite, alumina, titanium oxide, magnesia or polysiloxane.

The crosslinked polystyrene may be composed mainly of a crosslinked copolymer of a monovinyl aromatic compound such as styrene, divinylbenzene, vinylxylene or vinylnaphthalene with a polyvinyl aromatic compound such as divinylbenzene, divinyltoluene, divinylxylene, divinylnaphthalene, trivinylbenzene, bisvinyldiphenyl or bisbiphenylethane, or may be a copolymer of such a copolymer with a methacrylate such as glycerol methacrylate or ethylene glycol dimethacrylate.

Among such insoluble carriers, preferred is silica gel or alumina in view of the cost and availability.

The form of the insoluble carrier may be any form commonly employed as a separation substrate, such as spheres (for example, spherical particles), particles, fibers, granules, monolith columns, hollow fibers or a membrane (for example, flat membrane), and is not particularly limited. Among them, the form of spheres, a membrane, particles or fibers is preferred. The form of particles is particularly preferred, since the volume of use can optionally be set when used for a column method or a batch method.

The particle size of the support is usually an outer diameter of from 1 μm to 10 mm, and is preferably from 2 μm to 1 mm in view of the precious metal ion adsorption performance and handling efficiency. The support may be either porous or non-porous, and is preferably porous, whereby the effective area for the precious metal ion adsorption is larger.

The method of fixing the ligand to adsorb precious metal ions on the support is not particularly limited, and may, for example, be a method wherein it is physically adsorbed and supported or a fixation method by chemical bond.

The commercially available precious metal ion adsorbent and the precious metal ion adsorbent having an optional ligand fixed on a carrier are not particularly limited, and they may be used, for example, for a column method or a batch method, and in the case of a column method, they may be used for a packed bed or an extension bed.

In the present invention, in a case where the precious metal to be recovered is palladium, an amide-containing sulfide compound represented by the formula (II) is particularly suitably used as the extracting agent or adsorbent of palladium ions:

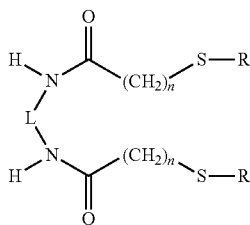

wherein two R's are each independently a methyl group, an ethyl group, a $C_{3-18}$, preferably $C_{6-12}$ chain hydrocarbon group, a $C_{3-10}$, preferably $C_{6-10}$ alicyclic hydrocarbon group, or a $C_{6-14}$, preferably $C_{6-10}$ aromatic hydrocarbon group.

The $C_{3-18}$, preferably $C_{6-12}$ chain hydrocarbon group is not particularly limited and may, for example, be a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group (cetyl group), a heptadecyl group, an octadecyl group (stearyl group), an oleyl group, an elaidyl group, an isopropyl group, an isobutyl group, a sec-butyl group, a tert-butyl group, an isopentyl group, a neopentyl group, a tert-pentyl group, a 2-ethylhexyl group, a vinyl group, an allyl group, a 1-propenyl group, an isopropenyl group, a 1-butenyl group, a 2-butenyl group, a 2-methylallyl group, a 1-heptynyl group, a 1-hexenyl group, a 1-heptenyl group, a 1-octenyl group or a 2-methyl-1-propenyl group.

The $C_{3-10}$ alicyclic hydrocarbon group is not particularly limited and may, for example, be a cyclopropyl group, a cyclobutyl group, a cyclopentyl group, a cyclohexyl group, a cycloheptyl group, a cyclooctyl group, a cyclononyl group, a cyclodecyl group, a cyclohexenyl group, a cyclohexadienyl group, a cyclooctenyl group or a cyclooctadienyl group.

The $C_{6-14}$ aromatic hydrocarbon group is not particularly limited and may, for example, be a phenyl group, a naphthyl group, an anthryl group, a tolyl group, a xylyl group, a cumenyl group, a benzyl group, a phenethyl group, a styryl group, a cinnamyl group, a biphenyl group or a phenanthryl group.

In the above formula (II), n's are each independently an integer of from 1 to 4, preferably from 1 to 2. L is a methylene group, an ethylene group, a $C_{3-8}$, preferably $C_{3-6}$ linear, branched or cyclic alkylene group or a $C_{6-14}$, preferably $C_{6-10}$ arylene group.

The $C_{3-8}$ linear or branched alkylene group is not particularly limited and may, for example, be a propylene group, a butylene group, a pentylene group, a hexylene group, a heptylene group or an octylene group, and they may be linear or branched. The position of the substituent is not particularly limited.

The $C_{3-8}$ cyclic alkylene group may, for example, be a cyclopropylene group, a cyclobutylene group, a cyclopentylene group, a cyclohexylene group, a cycloheptylene group, a cyclooctylene group, a cyclohexenylene group, a cyclohexadienylene group, a cyclooctenylene group or a cyclooctadienylene group. The position of the substituent is not particularly limited.

Further, the $C_{6-14}$ arylene group may, for example, be a phenylene group, a naphthylene group, an anthrylene group, a tolylene group, a xylylene group, a cumenylene group, a benzenylene group, a phenethylene group, a styrylene group, a cinnamylene group, a biphenylene group or a phenanthrylene group. The position of the substituent is not particularly limited.

Among them, L is preferably a 1,2-ethylene group, a 1,3-propylene group, a 1,4-butylene group, a 1,2-cyclohexylene group or a 1,2-phenylene group, particularly preferably a 1,3-propylene group or a 1,2-phenylene group, whereby high palladium ion adsorption performance will be obtained.

The amide-containing sulfide compound represented by the formula (II) may be produced, for example, as follows, although its production process is not particularly limited. That is, a compound represented by the following formula (3):

wherein L is the same group as in the formula (II), is reacted with a compound represented by the following formula (4):

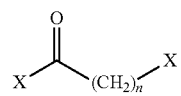

wherein n is the same integer as in the formula (II), and X's are each independently a halogen atom, in the presence of a base to obtain a compound represented by the following formula (5):

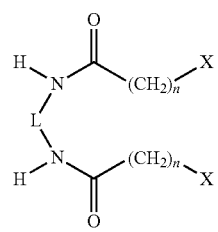

wherein L is the same group as in the formula (II), n is the same integer as in the formula (II), and X is a halogen atom.

Then, the compound represented by the formula (5) and thiobenzoic acid are reacted in the presence of a base to obtain a compound represented by the following formula (6):

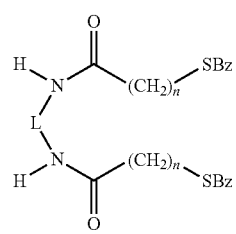

wherein Bz is a benzoyl group, L is the same group as in the formula (II), and n is the same integer as in the formula (II).

Then, the compound represented by the formula (6) and a compound represented by the following formula (7) are reacted in the presence of a base to obtain the amide-containing sulfide compound represented by the formula (II):

$$R-Y \qquad (7)$$

wherein R is the same group as in the formula (II), and Y is a halogen atom.

The compound represented by the formula (3) is not particularly limited and may, for example, be 1,2-diaminoethane, 1,3-diaminopropane, 1,4-diaminobutane, 1,6-diaminohexane, 1,2-diaminocyclohexane or 1,2-phenylenediamine.

In the compound represented by the formula (4), X is a halogen atom. The halogen atom is not particularly limited, and is preferably chlorine, bromine or iodine.

The compound represented by the formula (4) is not particularly limited and may, for example, be chloroacetyl chloride, 3-chloropropionyl chloride, 4-chlorobutyryl chloride or 5-chlorovaleryl chloride.

In the compound represented by the formula (5), X is a halogen atom. The halogen atom is not particularly limited and is preferably chlorine, bromine or iodine.

In the compound represented by the formula (7), Y is a halogen atom. The halogen atom is not particularly limited, and is preferably chlorine, bromine or iodine.

The compound represented by the formula (7) is not particularly limited and may, for example, be bromoethane, bromopropane, bromobutane, bromohexane or bromodecane.

As described above, the amide-containing sulfide compound represented by the formula (II) can be prepared by reacting the compound represented by the formula (6) and the compound represented by the formula (7) in the presence of a base.

In the reaction to produce the amide-containing sulfide compound represented by the formula (II), the base to be used is not particularly limited and may, for example, be an inorganic base such as sodium hydroxide, potassium hydroxide, sodium carbonate, potassium carbonate, sodium acetate or potassium acetate, a tertiary amine such as triethylamine or triethylenediamine, or an organic metal such as lithium diethylamide, lithium (isopropyl)cyclohexylamide, lithium-bis(dimethylsilyl)amide, lithium diisopropylamide, triphenylmethane lithium, or lithium (2,2,6,6-tetramethyl)piperidine amide. As such a base, a commercially available reagent may be used as it is. The amount of use of the base is not particularly limited, and for example, selected from a range of from 1.8 to 20 molar times to 1 mol of the compound represented by the formula (6), preferably from 1.8 to 10 molar times. The reaction will sufficiently proceed within a range of from 1.8 to 20 molar times, and a range of from 1.8 to 10 molar times is economically preferred.

The reaction for production of the amide-containing sulfide compound represented by the formula (II) is carried out usually in a solvent. The solvent is not particularly limited so long as it will not impair the reaction, and is preferably an alcohol solvent such as methanol, ethanol or isopropanol, an ether solvent such as diethyl ether, tetrahydrofuran, dimethoxyethane or cyclopentyl methyl ether, an aromatic hydrocarbon solvent such as benzene, toluene or xylene, or a mixed solvent of such an organic solvent with water. The amount of use of the solvent is not particularly limited and is usually from 2 to 40 times by weight to the compound represented by the formula (6).

The reaction temperature in the production of the amide-containing sulfide compound is preferably within a range of from −78 to 100° C., and in view of the operation efficiency and economical efficiency, more preferably from −10 to 50° C.

The reaction time in the production of the amide-containing sulfide compound represented by the formula (II) varies depending upon the concentration of the compound represented by the formula (6) and the base, the reaction temperature and the like, and is usually within a range of from several minutes to 24 hours.

The amide-containing sulfide compound can be separated from other components in the reaction liquid by a liquid separation operation. Further, it can be purified to have high purity by e.g. recrystallization or silica gel chromatography.

The amide-containing sulfide compound can be used as a palladium ion extracting agent or adsorbent. For example, in a case where the amide-containing sulfide compound is a solid, it can be used as a palladium ion adsorbent as it is. In a case where the amide-containing sulfide compound is a liquid, it can be used as a palladium ion extracting agent as it is. The amide-containing sulfide compound can be used as an extracting agent, as dissolved in a solvent. Further, the amide-containing sulfide compound may be fixed on an optional carrier by an optional method and is used as an adsorbent.

In a case where the amide-containing sulfide compound represented by the formula (II) is used as the palladium ion extracting agent, the amide-containing sulfide compound may be used as dissolved in an organic solvent. The concentration of the amide-containing sulfide compound represented by the formula (II) is selected within a range of from 1 to 99 wt %, and is preferably within a range of from 10 to 50 wt % in view of the operation efficiency.

The organic solvent in which the amide-containing sulfide compound represented by the formula (II) is dissolved is not particularly limited, and may, for example, be an aliphatic hydrocarbon solvent such as n-hexane or cyclohexane, an ether solvent such as diethyl ether or diisopropyl ether, a halogenated hydrocarbon solvent such as methylene chloride or chloroform, or an aromatic hydrocarbon solvent such as benzene, toluene or xylene.

In a case where the amide-containing sulfide compound is used as the palladium ion adsorbent, the carrier on which the amide-containing sulfide compound is fixed is not particularly limited so long as it is insoluble in water. The carrier to be used is not particularly limited and may, for example, be a polymer carrier such as a styrene polymer such as polystyrene or crosslinked polystyrene, a polyolefin such as polyethylene or polypropylene, a poly(halogenated olefin) such as polyvinyl chloride or polytetrafluoroethylene, a nitrile polymer such as polyacrylonitrile, a (meth)acrylic polymer such as polymethyl methacrylate or polyethyl acrylate, or a high molecular weight polysaccharide such as cellulose, agarose or dextran, or an inorganic carrier such as activated carbon, silica gel, diatomaceous earth, hydroxyapatite, alumina, titanium dioxide, magnesia or polysiloxane.

Here, the crosslinked polystyrene is composed mainly of a crosslinked copolymer of a monovinyl aromatic compound such as styrene, vinyltoluene, vinylxylene or vinylnaphthalene with a polyvinyl aromatic compound such as divinylbenzene, divinyltoluene, divinylxylene, divinylnaphthalene, trivinylbenzene, bisvinyldiphenyl or bisvinylphenylethane, or may be a copolymer of such a copolymer with a methacrylate such as glycerol methacrylate or ethylene glycol dimethacrylate. Among these carriers, particularly preferred is alumina or silica gel in view of availability and the cost.

The form of the carrier to be used in the present invention may be any form commonly used as a separation substrate such as spheres (for example, spherical particles), particles, fibers, granules, monolith columns, hollow fibers or a membrane (for example, flat membrane), and is not particularly limited, and among them, the form of spheres, a membrane, particles, granules or fibers is preferred. The support in the form of spheres, particles or granules is particularly preferred, since the volume of use can freely be set when used for a column method or a batch method.

The particle size of the support in the form of spheres, particles or granules is usually an average particle size within a range of from 1 μm to 10 mm, preferably within a range of from 2 μm to 1 mm.

The carrier may be porous or non-porous. The average pore size of the porous carrier is usually from 1 nm to 1 μm, preferably within a range of from 1 nm to 300 nm in view of the palladium ion adsorption amount.

The method of fixing the amide-containing sulfide compound represented by the formula (II) on the carrier is not particularly limited and may, for example, be a method such that the amide-containing sulfide compound is physically adsorbed and fixed on the carrier, or a method such that the amide-containing sulfide compound is chemically bonded to and fix on the carrier.

The method of physical adsorption and fixation is not particularly limited and may, for example, be a method such that the amide-containing sulfide compound is dissolved in a solvent such as dichloromethane, the above carrier is added, the carrier is impregnated with the amide-containing sulfide compound, and the solvent is distilled off.

The method of chemical bonding and fixation is not particularly limited and may, for example, be a method such that polychloromethylstyrene (PCMS) and the amide-containing sulfide compound are reacted in the presence of a base.

The fixation ratio of the amide-containing sulfide compound on the carrier may optionally be adjusted depending upon the purpose and is not particularly limited, and the amide-containing sulfide compound is preferably within a range of from 1 to 50 wt %, more preferably from 5 to 30 wt %.

In the present invention, the aqueous solution containing precious metal ions particularly palladium ions to be brought into contact with the extracting agent or the adsorbent is not particularly limited and may, for example, be an aqueous solution in which an automobile exhaust gas purifying catalyst or jewelry is dissolved, or a solution after acid leaching in a step of wet refining of platinum group metals.

Such an aqueous solution containing precious metal ions particularly palladium ions may contain base metal ions such as copper ions, iron ions, nickel ions or zinc ions in addition to platinum group metal ions such as palladium ions, platinum ions or rhodium ions.

The pH of the aqueous solution containing precious metal ions particularly palladium ions is not particularly limited, and for example, the aqueous solution is preferably acidic. The acid used here is not particularly limited and may, for example, be an inorganic acid such as hydrochloric acid, sulfuric acid or nitric acid. Among them, hydrochloric acid is particularly preferred.

The acid concentration of the aqueous solution containing precious metal ions particularly palladium ions is not particularly limited, and is preferably within a range of from 0.1 to 5 mol/L. At the acid concentration within such a range, separation of precious metal ions particularly palladium ions can be carried out without impairing the adsorption efficiency of precious metal ions particularly palladium ions.

In the present invention, the amount of use of the extracting agent or adsorbent is preferably, for example, an equimolar amount or more, as calculated as the amide-containing sulfide compound represented by the formula (II), relative to precious metal ions particularly palladium ions in the aqueous solution containing precious metal ions particularly palladium ions.

In the extraction or adsorption using the extracting agent or adsorbent, a mixture of the solution containing precious metal ions particularly palladium ions is preferably stirred. By stirring, the adsorption of the precious metal ions tends to be accelerated. Further, in a case where the adsorbent is used, the aqueous solution containing precious metal ions may be made to flow through the palladium ion adsorbent packed in a fixed bed such as a column so that they are contacted with each other.

The amount of use of the back-extracting agent or desorbent is not particularly limited, and is, for example, selected from 2 to 10,000 molar times to 1 mol of the extracting agent or desorbent to be used, for example, the amide-containing sulfide compound represented by the formula (II), and is preferably from 5 to 1,000 molar times.

In the present invention, a mixture of the palladium ion extracting agent into which the precious metal ions are extracted and the back-extracting agent, or a mixture of the palladium ion adsorbent in which the precious metal ions are adsorbed and the desorbent, is preferably stirred, since the back extraction or desorption of the precious metal ions is accelerated by stirring. Further, in a case where the adsorbent in which the precious metal ions are adsorbed is used, the desorbent may be made to flow through the adsorbent packed in a fixed bed such as a column, so that they are contacted with each other.

EXAMPLES

Now, the present invention will be described in detail with reference to Examples. However, it should be understood that the present invention is by no means restricted to such specific Examples.

$^1$H-NMR (nuclear magnetic resonance) was measured by Gemini-200 (manufactured by Varian).

Aqueous solutions of metal ions were prepared by diluting commercially available palladium standard solution (1,000 ppm), platinum standard solution (1,000 ppm), rhodium standard solution (1,000 ppm), copper standard solution (1,000 ppm), iron standard solution (1,000 ppm), nickel standard solution (1,000 ppm) and zinc standard solution (1,000 ppm).

The palladium ion concentration and the metal palladium purity in the aqueous solution were measured by an ICP emission spectrometer (OPTIMA3300DV, manufactured by PerkinElmer Co., Ltd.).

The sulfur content was measured by an ion chromatography method. The ion chromatography measurement was carried out after the following pretreatment in the following facility under the following conditions.

Pretreatment: A sample was introduced into an automatic sample combustion apparatus (AQF-100, manufactured by Mitsubishi Chemical Analytech Co., Ltd.), and $SO_4^{2-}$ formed by combustion was collected in an adsorption liquid (internal standard substance $PO_4$—).

Measurement apparatus: IC-2001 manufactured by TOSOH CORPORATION

Separation column: TSKgel Super IC-AP (4.6 mm in diameter×150 mm)

Detector: Electrical conduction detector

Eluent: 2.7 mmol/L $NaHCO_3$+1.8 mmol/L $Na_2CO_3$

As the sulfur-containing amino acid derivative represented by the formula (I), commercially available DL-methionine (manufactured by KISHIDA CHEMICAL Co., Ltd.) was used as it was.

Synthetic Example 1

Synthesis of Compound (7)

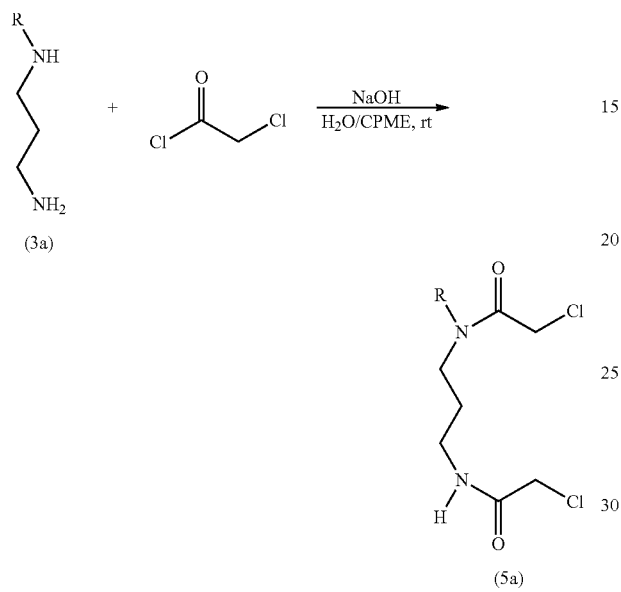

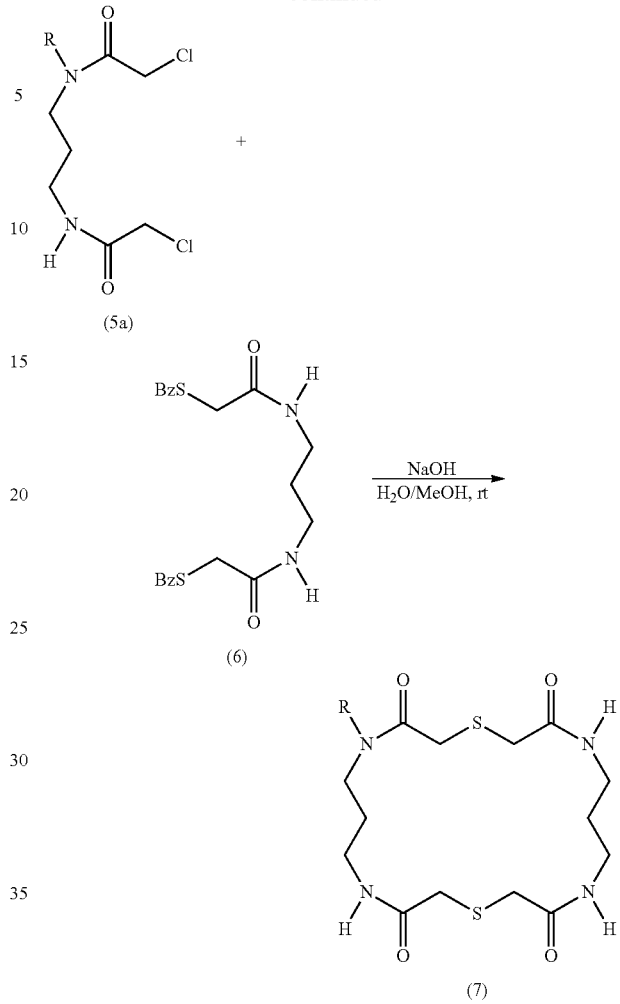

In the formulae (3a), (5a) and (7), R is a long chain alkyl group (such as a cetyl group, a stearyl group or an oleyl group) derived from beef tallow.

Synthesis of Diacylated Form (5a)

Into a 200 mL eggplant flask, 9.51 g (30 mmol) of beef tallow propylenediamine (3a) (manufactured by Kao Corporation, tradename: Diamine RRT), 30.00 g (75 mmol) of a 10 wt % sodium hydroxide aqueous solution and 40 g of diethyl ether were put. Into this mixture, 8.47 g (75 mmol) of chloroacetyl chloride was dropwise added at room temperature over a period of 2 hours, followed by stirring at room temperature further for 30 minutes. The reaction liquid was put in a separatory funnel and extracted with ethyl acetate (15 mL×2). The organic layer fractions were put together and sequentially washed with 15 mL of a saturated sodium bicarbonate solution and 15 mL of a saturated sodium chloride solution. After dehydration over sodium sulfate, the solvent was distilled off under reduced pressure to obtain a diacylated form represented by the above formula (5a) (hereinafter referred to as diacylated form (5a)) in an amount of 12.59 g with a yield of 89.3%.

$^1$H-NMR (CDCl$_3$) δ (ppm): 0.85-0.91 (m, peak attributable to the beef tallow alkyl group), 1.25-1.31 (m, peak attributable to the beef tallow alkyl group), 1.52-1.80 (m, peak attrib-

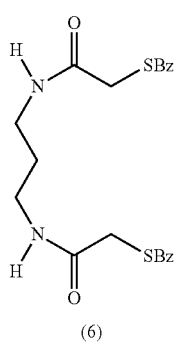

utable to the beef tallow alkyl group), 1.96-2.05 (m, peak attributable to the beef tallow alkyl group), 3.22-3.48 (m, 6H), 4.04 (s, 2H), 4.08 (s, 2H), 5.32-5.38 (m, peak attributable to the beef tallow alkyl group), 7.59 (1H, brs), undetected 2H (estimated to be overlapping with the peak attributable to the beef tallow alkyl group)

Synthesis of Diacylated Form (5b)

Into a 200 mL eggplant flask, 3.71 g (50 mmol) of 1,3-propanediamine (3a), 50 g of water and 20 g of diethyl ether were weighted, and 24.00 g (120 mmol) of a 20 wt % sodium hydroxide aqueous solution was added. To the mixture, 13.55 g (120 mmol) of chloroacetyl chloride was dropped at 0° C. over a period of one hour, followed by stirring at 0° C. further for one hour. The formed white solid was collected by filtration and sequentially washed with water and diethyl ether to obtain a diacylated form represented by the above formula (5b) (hereinafter referred to as diacylated form (5b)) in an amount of 10.41 g with a yield of 91.7%.

$^1$H-NMR (DMSO-$d_6$) δ (ppm): 1.55 (2H, quintet, J=7.0 Hz), 3.03-3.10 (4H, m), 4.03 (4H, s), 8.22 (2H, brs)

Synthesis of Dithioesterified Form (6)

Into a 100 mL eggplant flask, 2.65 g (19.2 mmol) of potassium carbonate and 40 g of water were weighed, and 2.65 g (19.2 mmol) of thiobenzoic acid was added, followed by stirring at 40° C. for 30 minutes. To the mixture, 1.82 g (8 mmol) of the above diacylated form (5b) and 10 g of tetrahydrofuran were added, followed by stirring at 40° C. for 3 hours. Then, stirring was carried out at 0° C. further for one hour, and the formed white solid was collected by filtration and washed with water to obtain a dithioesterified form represented by the above formula (6) (hereinafter referred to as dithioesterified form (6a)) in an amount of 3.51 g with a yield of 95.6%.

$^1$H-NMR (CDCl$_3$) δ (ppm): 1.65 (2H, quintet, J=6.2 Hz), 3.23-3.32 (4H, m), 3.74 (4H, s), 6.88 (2H, brs), 7.43-7.52 (4H, m), 7.57-7.66 (2H, m), 7.95-8.00 (4H, m)

Synthesis of Compound (7)

Into a 300 mL eggplant flask, 11.53 g (26.8 mmol) of the above dithioesterified form (6) and 100 g of methanol were weighed, and 10.71 g (53.5 mmol) of a 20 wt % sodium hydroxide aqueous solution was added, followed by stirring in a stream of nitrogen at room temperature for 2 hours. To the mixture, 1.14 g (5 mmol) of the above diacylated form (5a) was added, followed by stirring at room temperature for 20 hours. The solvent was distilled off under reduced pressure, and 30 g of tetrahydrofuran, 30 g of water and 10.71 g (53.5 mmol) of a 20 wt % sodium hydroxide aqueous solution were added, followed by stirring at 40° C. for one hour. The reaction liquid was put into a separatory funnel and extracted with ethyl acetate (20 mL×3). The organic layer fractions were put together and sequentially washed with 20 mL of a saturated sodium bicarbonate solution and 20 mL of a saturated sodium chloride solution. After dehydration over sodium sulfate, the solvent was distilled off under reduced pressure to obtain compound (7) in an amount of 15.40 g with a yield of 92.9%.

$^1$H-NMR (CDCl$_3$) δ (ppm): 0.85-0.91 (m, peak attributable to the beef tallow alkyl group), 1.25-1.31 (m, peak attributable to the beef tallow alkyl group), 1.50-2.03 (m, peak attributable to the beef tallow alkyl group), 3.26-3.52 (m, 18H), 5.32-5.38 (m, peak attributable to the beef tallow alkyl group), 7.36 (1H, brs), 7.58 (1H, brs), 7.70 (1H, brs), undetected 4H (estimated to be overlapping with the peak attributable to the beef tallow alkyl group)

Synthetic Example 2

Synthesis of Compound (9)

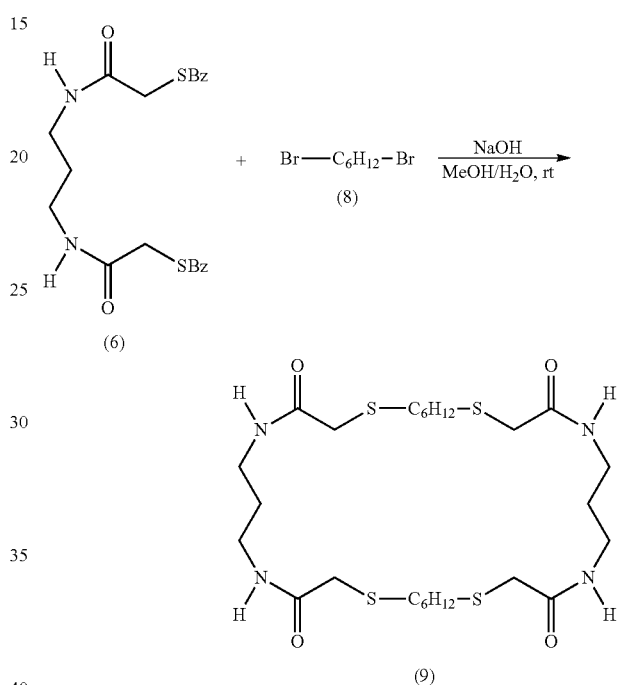

Into a 50 mL eggplant flask, 2.15 (5 mmol) of the above dithioesterified form (6) and 20 g of methanol were weighed, and 2.00 g (10 mmol) of a 20 wt % sodium hydroxide aqueous solution was added, followed by stirring in a stream of nitrogen at room temperature for 2 hours. To the mixture, 1.22 g (5 mmol) of 1,6-dibromohexane (8) was added, followed by stirring at room temperature for 20 hours. The formed white solid was collected by filtration and sequentially washed with water and methanol to obtain compound (9) in an amount of 1.16 g with a yield of 76.3%.

$^1$H-NMR (DMSO-$d_6$) δ (ppm): 1.34-1.39 (8H, m), 1.50-1.63 (12H, m), 2.55-2.61 (8H, m), 3.05-3.17 (16H, m), 8.02 (4H, brs)

Synthetic Example 3

Synthesis of Compound (15)

As an example for synthesis of the extracting agent of palladium ions as disclosed in Claims of Patent Document 2 as a Comparative Example, synthesis of N,N-diethyl-3-thioundecaneamide (hereinafter referred to as compound (15)) is shown below.

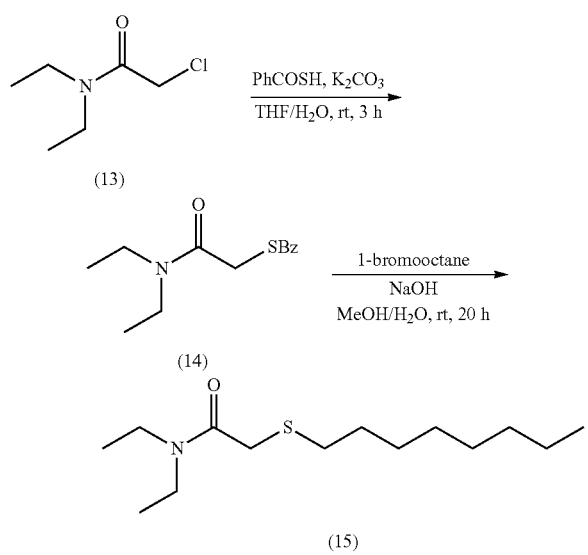

Synthesis of Thioesterified Form (14)

Into a 200 mL eggplant flask, 15.20 g (110 mmol) of potassium carbonate and 80 g of water were weighed, and 15.20 g (110 mmol) of thiobenzoic acid was added, followed by stirring at room temperature for 30 minutes. To the mixture, 14.96 g (100 mmol) of 2-chloro-N,N-diethylacetamide (13) and 20 g of tetrahydrofuran were added, followed by stirring at room temperature for 3 hours. The reaction liquid was put into a separatory funnel and extracted with ethyl acetate (10 mL×2). The organic layer fractions were put together and sequentially washed with 10 mL of water and 10 mL of a saturated sodium hydrogen solution. After dehydration over sodium sulfate, the solvent was distilled off under reduced pressure to obtain compound (14) in an amount of 25.67 g with a yield of 100%.

$^1$H-NMR (CDCl$_3$) δ (ppm): 1.15 (3H, t, J=7.2 Hz), 1.28 (3H, t, J=7.2 Hz), 3.27 (2H, S), 3.37-3.50 (4H, m), 7.41-7.49 (2H, m), 7.55-7.63 (1H, m), 7.97-8.01 (2H, m)

Synthesis of Compound (15)

Into a 100 mL eggplant flask, 1.26 g (5 mmol) of the above thioesterified form (14) and 20 g of methanol were weighted, and 1.00 g (5 mmol) of a 20 wt % sodium hydroxide aqueous solution was added, followed by stirring in a stream of nitrogen at room temperature for 2 hours. To the mixture, 0.97 g (5 mmol) of 1-bromooctane was added, followed by stirring at room temperature for 20 hours. The solvent was distilled off under reduced pressure, and 10 g of tetrahydrofuran, 10 g of water and 1.00 g (5 mmol) of a 20 wt % sodium hydroxide aqueous solution were added, followed by stirring at 40° C. for one hour. The reaction solution was put into a separatory funnel and extracted with ethyl acetate (10 mL×2). The organic layer fractions were put together and sequentially washed with 10 mL of a saturated sodium bicarbonate solution, 10 mL of water and 10 mL of a saturated sodium chloride solution. After dehydration over sodium sulfate, the solvent was distilled off under reduced pressure to obtain compound (15) in an amount of 1.28 g with a yield of 98.5%.

$^1$H-NMR (CDCl$_3$) δ (ppm): 0.87 (3H, t, J=7.0 Hz), 1.09-1.43 (16H, m), 1.54-1.68 (2H, m), 2.65 (2H, t, J=7.2 Hz), 3.27 (2H, s), 3.37 (4H, q, J=7.0 Hz)

Preparation Example 1

Fixation of Compound (7) on Alumina Carrier

Into a 50 mL eggplant flask, 0.1 g of compound (7) prepared in Synthetic Example 1 and 0.9 g of tetrahydrofuran were weighed, followed by stirring at 40° C. for 30 minutes. Then, 0.9 g of alumina (manufactured by Wako Pure Chemical Industries, Ltd., tradename: Alumina, Activated) was added, followed by stirring at 40° C. further for 30 minutes. The solvent was distilled off under reduced pressure, and the obtained white powder was dried under reduced pressure at room temperature to prepare alumina having compound (7) in a ratio of 10 wt % supported by impregnation, which is regarded as adsorbent A.

Preparation Example 2

Fixation of Compound (9) on Alumina Carrier

Into a 50 mL eggplant flask, 0.1 g of compound (9) synthesized in Synthetic Example 2, 9 mL of chloroform and 1 mL of methanol were weighed, followed by stirring at 40° C. for 30 minutes. Then, 0.9 g of alumina (manufactured by Wako Pure Chemical Industries, Ltd., tradename: Alumina, Activated) was added, followed by stirring at 40° C. further for 30 minutes. The solvent was distilled off under reduced pressure, and the obtained white powder was dried under reduced pressure at room temperature to prepare alumina having compound (9) in a ratio of 10 wt % supported by impregnation, which is regarded as adsorbent B.

Example 1

Synthesis of Compound (10)

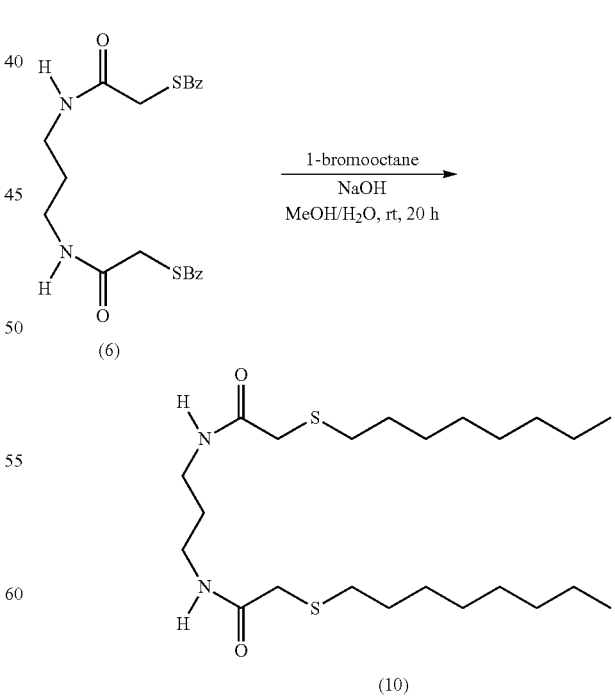

Into a 100 mL eggplant flask, 2.15 g (5 mmol) of the above dithioesterified form (6) and 20 g of methanol were weighed, and 2.00 g (10 mmol) of a 20 wt % sodium hydroxide aqueous solution was added, followed by stirring in a stream of nitrogen at room temperature for 2 hours. To the mixture, 1.93 g (10 mmol) of 1-bromooctane was added, followed by stirring at room temperature for 20 hours. The solvent was distilled off under reduced pressure, and 10 g of tetrahydrofuran, 10 g of water and 2.00 g (10 mmol) of a 20 wt % sodium hydroxide aqueous solution were added, followed by stirring at 40° C. for one hour. The reaction solution was put into a separatory funnel and extracted with ethyl acetate (10 mL×2). The organic layer fractions were put together and sequentially washed with 10 mL of a saturated sodium bicarbonate solution, 10 mL of water and 10 mL of a saturated sodium hydrogen solution. After dehydration over sodium sulfate, the solvent was distilled off under reduced pressure to obtain compound (10) in an amount of 2.12 g with a yield of 95.1%.

$^1$H-NMR (CDCl$_3$) δ (ppm): 0.88 (6H, t, J=7.0 Hz), 1.27-1.38 (20H, m), 1.52-1.79 (6H, m), 2.54 (4H, t, J=7.0 Hz), 3.23 (4H, s), 3.29-3.83 (4H, m), 7.32 (2H, brs)

Example 2

300 mg (dry weight) of adsorbent A prepared in Preparation Example 1 was added into 10 mL of a 1 mol/L hydrochloric acid solution containing 500 mg/L of palladium ions, followed by stirring at room temperature for 2 hours. The solution was subjected to filtration through a membrane filter having a pore size of 0.45 μm, and from the remaining palladium ion concentration in the filtrate and the initial concentration, the palladium ion adsorption amount was calculated as 16.6 mg per 1 g of adsorbent.

Then, the adsorbent collected by filtration was washed with water and dried. 30 mg of the dried adsorbent was added into 10 mL of a desorbent prepared as a 1 mol/L hydrochloric acid aqueous solution with a DL-methionine concentration of 10 wt %, followed by stirring at room temperature for one hour. Then, the solution was subjected to filtration through a membrane filter having a pore size of 0.45 μm, and the palladium ion desorption amount was determined from the palladium ion concentration in the filtrate, whereupon the palladium ion desorption ratio was 100%.

Example 3

The same operation as in Example 2 was carried out except that the DL-methionine concentration was 2 wt %, whereupon the palladium ion desorption ratio was 98%.

Example 4

The same operation as in Example 2 was carried out except that the DL-methionine concentration was 1 wt %, whereupon the palladium ion desorption ratio was 84%.

Example 5

400 mg (dry weight) of adsorbent B prepared in Preparation Example 2 was added into 10 mL of a 1 mol/L hydrochloric acid solution containing 500 mg/L of palladium ions, followed by stirring at room temperature for 2 hours. The solution was subjected to filtration through a membrane filter having a pore size of 0.45 μm, and from the remaining palladium ion concentration in the filtrate and the initial concentration, the palladium ion adsorption amount was calculated as 12.5 mg per 1 g of adsorbent.

Then, the adsorbent collected by filtration was washed with water and dried. 40 mg of the dried adsorbent was added into 10 mL of a desorbent prepared as a 1 mol/L hydrochloric acid aqueous solution with a DL-methionine concentration of 10 wt %, followed by stirring at room temperature for one hour. Then, the solution was subjected to filtration through a membrane filter having a pore size of 0.45 μm, and the palladium ion desorption amount was determined from the palladium ion concentration in the filtrate, whereupon the palladium ion desorption amount was 100%.

Example 6

200 mg (dry weight) of SiliaBond TAAcOH (adsorbent) manufactured by SILICYCLE was added to 10 mL of a 1 mol/L hydrochloric acid solution containing 500 mg/L of palladium ions, followed by stirring at room temperature for 2 hours. Then, the solution was subjected to filtration through a membrane filter having a pore size of 0.45 μm, and from the remaining palladium ion concentration in the filtrate and the initial concentration, the palladium ion adsorption amount was calculated as 19.5 mg per 1 g of adsorbent.

Then, the adsorbent collected by filtration was washed with water and dried, and 20 mg of the adsorbent was added to 10 mL of desorbent prepared as a 1 mol/L hydrochloric acid aqueous solution with a DL-methionine concentration of 10 wt %, followed by stirring at room temperature for one hour. Then, the solution was subjected to filtration through a membrane filter having a pore size of 0.45 μm, and the palladium ion desorption amount was determined from the palladium ion concentration in the filtrate, whereupon the desorption ratio of palladium ions was 100%.

Example 7

30 mg of compound (10) was dissolved in 2 mL of dichloromethane to prepare extracting agent A. Extracting agent A and 10 mL of a 1 mol/L hydrochloric acid solution containing 500 mg/L of palladium ions were mixed and stirred at room temperature for 1 hour. The aqueous phase and the organic phase were separated by a separately funnel. From the remaining palladium ion concentration in the aqueous phase and the initial concentration, the amount of extracted palladium ions was calculated as 166 mg per 1 g of extracting agent A.

Then, to the separated organic phase, 10 mL of a 1 mol/L hydrochloric acid aqueous solution having 1 g of DL-methionine dissolved (back-extracting agent) was added, followed by stirring at room temperature for one hour, and the aqueous phase and the organic phase were separated by a separatory funnel. The ratio of back-extraction of palladium ions determined from the palladium ion concentration in the obtained aqueous phase was 88%.

Example 8

Into 100 mL of a 1.5 wt % DL-methionine aqueous solution containing 100 mg/L of palladium ions (pH 7, prepared by diluting commercially available palladium standard solution (1,000 ppm) with water), an anode (electrode area: 20 cm$^2$) and a cathode (electrode area: 20 cm$^2$) each made of carbon were inserted, and a 1 A (ampere) constant current (current density: 10 A/dm$^2$) was applied at room temperature for one hour to carry out reduction by electrolysis, whereupon a black precipitate was obtained. The black precipitate was isolated by filtration using filter paper. As a result of ICP emission spectroscopy measurement and ion chromatography measurement, the black precipitate was metal palladium with a purity of 99 wt % or higher.

Example 9

To 100 mL of a 1 mol/L hydrochloric acid aqueous solution containing 100 mg/L of palladium ions and 1.5 wt % of DL-methionine (prepared by using commercially available palladium chloride), sodium hydroxide was added until the solution became neutral. Into the obtained solution, an anode (electrode area: 20 cm$^2$) and a cathode (electrode area: 20 cm$^2$) each made of carbon were inserted, and a 1 A (ampere) constant current (current density: 10 A/dm$^2$) was applied at room temperature for one hour to carry out reduction by electrolysis, whereupon a black precipitate was obtained. The black precipitate was isolated by filtration using filter paper. As a result of ICP emission spectroscopy measurement and ion chromatography measurement, the black precipitate was metal palladium with a purity of 99 wt % or higher.

Example 10

Preparation of Adsorbent C

In a 50 mL eggplant flask, 0.25 g of compound (10) was dissolved in 5 mL of dichloromethane, and 0.75 g of silica gel (manufactured by FUJI SILYSIA CHEMICAL LTD, tradename: MB5D 200-350) was added, followed by stirring at 40° C. further for 30 minutes. The solvent was distilled off under reduced pressure, and the obtained white powder was dried under reduced pressure at room temperature to prepare silica gel having compound (10) in a ratio of 25 wt % supported by impregnation (which is regarded as adsorbent C)

Example 11

Synthesis of Compound (12)

An amide-containing cyclic sulfide compound represented by the following formula (12) was prepared (amount: 1.22 g, yield from 1,2-phenylenediamine: 89.7%) in the same manner as in Synthetic Example 1 and Example 1 except that 5.41 g of 1,2-phenylenediamine was used instead of 1,3-propanediamine.

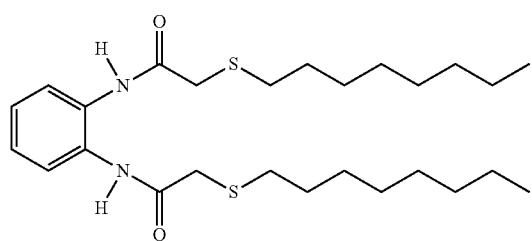

(12)

$^1$H-NMR (CDCl$_3$) δ (ppm): 0.88 (6H, t, J=7.0 Hz), 1.26-1.41 (20H, m), 1.56-1.66 (4H, m), 2.62 (4H, t, J=7.2 Hz), 3.39 (4H, s), 7.22-7.27 (2H, m), 7.53-7.58 (2H, m), 8.97 (2H, brs)

Example 12

Preparation of Adsorbent D

Silica gel having compound (12) in a ratio of 25 wt % supported by impregnation (which is regarded as adsorbent D) was prepared in the same manner as in Example 10 except that compound (12) was used instead of compound (10).

Example 13

Preparation of Adsorbent E

Silica gel having compound (12) in a ratio of 25 wt % supported by impregnation (which is regarded as adsorbent E) was prepared in the same manner as in Example 10 except that compound (12) was used instead of compound (10) and that MB4B 30-50 (manufactured by FUJI SILYSIA CHEMICAL LTD.) was used instead of MB5D 200-350 as silica gel.

Preparation Example 3

Preparation of Adsorbent F

Silica gel having compound (15) in a ratio of 25 wt % supported by impregnation (which is regarded as adsorbent F) was prepared in the same manner as in Example 10 except that compound (15) was used instead of compound (10).

Preparation Example 4

Preparation of Adsorbent G

Silica gel having compound (7) in a ratio of 25 wt % supported by impregnation (which is regarded as adsorbent G) was prepared in the same manner as in Example 10 except that compound (7) was used instead of compound (10).

Example 14

Separation of Palladium Ions Using Adsorbent C

Into 10 mL of a 1 mol/L hydrochloric acid solution containing 50 mg/L of palladium ions and 150 mg/L of platinum ions, 20 mg of adsorbent C was added, followed by stirring at room temperature for one hour. Then, the solution was subjected to filtration through a membrane filter having a pore size of 0.45 μm, and the remaining metal concentration in the filtrate was measured. From the remaining metal concentration and the initial concentration, adsorption ratios of the respective metals were determined, whereupon the palladium ion adsorption ratio was 87.6%, and the platinum ion adsorption ratio was 0%. On that occasion, the palladium ion adsorption amount was 21.9 mg per 1 g of adsorbent C, and the platinum ion adsorption amount was 0 mg per 1 g of adsorbent C, and palladium ions were high selectively adsorbed.

Example 15

Separation of Palladium Ions Using Adsorbent D

The same operation as in Example 14 was carried out except that 20 mg of adsorbent D was used instead of adsorbent C and as a result, the palladium ion adsorption ratio was 99.7% and the platinum ion adsorption ratio was 0%. On that occasion, the palladium ion adsorption amount was 24.9 mg per 1 g of adsorbent D and the platinum ion adsorption amount was 0 mg per 1 g of adsorbent D, and palladium ions were highly selectively adsorbed.

Example 16

Separation and Recovery of Palladium Ions Using Adsorbent E 0.2 g of adsorbent E was dispersed in water and packed in a column made of glass having an inner diameter of 5 mm and a length of 100 mm. 50 mL of a 1 mol/L hydrochloric acid solution (hereinafter referred to as a mobile phase) containing metal ions at a concentration as identified in Table 1 prepared by using a metal standard solution and a hydrochloric acid aqueous solution was passed from the top of the column at a flow rate of 36 mL/Hr to carry out adsorption of the metal ions. 20 mL of water was passed to rinse the column, and then 50 mL of a 3 mol/L hydrochloric acid solution containing DL-methionine with a concentration of 5 wt % was passed from the top of the column at a flow rate of 36 mL/Hr to carry out desorption of metal ions, and an eluent (hereinafter referred to as recovered liquid) was obtained from the bottom of the column. The metal concentration (unit: ppm) in the eluent was measured and the results are shown in Table 1. By the above operation, palladium ions were highly selectively separated and recovered. Further, the palladium ion adsorption amount was calculated from the palladium concentration in the recovered liquid, whereupon it was 38.0 mg per 1 g of adsorbent E.

TABLE 1

| Metal contained | Pd | Pt | Rh | Cu | Fe | Ni | Zn |
|---|---|---|---|---|---|---|---|
| Metal concentration in mobile phase (ppm) | 203 | 598 | 20 | 21 | 20 | 20 | 19 |
| Metal concentration in recovered liquid (ppm) | 152 | 1 | * | * | * | * | * |

* Lower than detection limit

Comparative Example 1

The same operation as in Example 5 was carried out except that 10 mL of a 28 wt % ammonia aqueous solution was used instead of the desorbent of the 1 mol/L hydrochloric acid aqueous solution with a DL-methionine concentration of 10 wt %, whereupon the palladium ion desorption ratio was 17%.

Comparative Example 2

The same operation as in Example 5 was carried out except that 10 mL of a 36 wt % hydrochloric acid aqueous solution was used instead of the desorbent of the 1 mol/L hydrochloric acid aqueous solution with a DL-methionine concentration of 10 wt %, whereupon the palladium ion desorption ratio was 14%.

Comparative Example 3

The same operation as in Example 8 was carried out except that 100 mL of a 3 wt % thiourea aqueous solution containing 100 mg/L of palladium (pH 7, prepared by diluting commercially available palladium standard solution (1,000 ppm) with water) was used as a test solution instead of the 1.5 wt % DL-methionine aqueous solution containing 100 mg/L of palladium ions, whereupon a large amount of a brown precipitate was formed. The brown precipitate was isolated by filtration using filter paper. As a result of ICP emission spectroscopy measurement, the palladium content in the brown precipitate was 2.9 wt %. Further, as a result of ion chromatography measurement, it was found that 91.9 wt % of sulfur was contained in the brown precipitate.

Comparative Example 4

The same operation as in Example 9 was carried out except that 100 mL of a 1 mol/L hydrochloric acid solution containing 100 mg/L of palladium ions and 3 wt % of thiourea (prepared by using commercially available palladium chloride) was used as a test solution instead of the 1 mol/L hydrochloric acid solution containing 100 mg/L of palladium ions and 1.5 wt % of DL-methionine, whereupon a large amount of a brown precipitate was formed. The brown precipitate was isolated by filtration using filter paper. As a result of ICP emission spectroscopy measurement, the palladium content in the brown precipitate was 2.9 wt %. Further, as a result of ion chromatography measurement, it was found that 93.0 wt % of sulfur was contained in the brown precipitate.

Comparative Example 5

Separation of Palladium Ions Using Adsorbent F

The same operation as in Example 14 was carried out except that 20 mg of adsorbent F was used instead of adsorbent C, whereupon the palladium ion adsorption ratio was 99.2% and the platinum ion adsorption ratio was 45.7%. On that occasion, the palladium ion adsorption amount was 24.8 mg per 1 g of adsorbent F and the platinum ion adsorption amount was 34.3 mg per 1 g of adsorbent F, and palladium ions could not highly selectively be adsorbed.

Comparative Example 6

Separation of Palladium Ions Using Adsorbent G

The same operation as in Example 14 was carried out except that 20 mg of adsorbent G was used instead of adsorbent C, whereupon the palladium ion adsorption ratio was 99.0% and the platinum ion adsorption ratio was 7.3%. On that occasion, the palladium ion adsorption amount was 24.8 mg per 1 g of adsorbent G and the platinum ion adsorption amount was 5.5 mg per 1 g of adsorbent G, and palladium ions could not highly selectively be adsorbed.

INDUSTRIAL APPLICABILITY

The back-extracting agent or desorbent of precious metal ions containing the sulfur-containing amino acid derivative of the present invention is capable of efficiently back-extracting or desorbing precious metal ions from various extracting agents or adsorbents, and further, by reducing a recovered liquid containing precious metal ions obtained, a high purity precious metal can be produced, and precipitated and recovered very easily. Accordingly, use in a resource recycle field of recovering and reusing expensive precious metals used in discarded industrial catalysts and automobile exhaust gas purifying catalysts, electric appliances, and the like, is expected.

The entire disclosures of Japanese Patent Application No. 2010-292588 filed on Dec. 28, 2010 and Japanese Patent Application No. 2011-037052 filed on Feb. 23, 2011 including specifications, claims, drawings and summaries are incorporated herein by reference in their entireties.

The invention claimed is:

1. A method for recovering a precious metal, which comprises bringing an extracting agent or adsorbent in which precious metal ions are extracted or adsorbed, into contact with a back-extracting agent or desorbent containing a sulfur-containing amino acid derivative represented by the following formula (I):

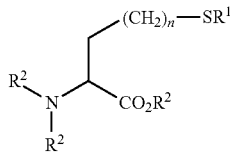

(I)

wherein $R^1$ is a methyl group, an ethyl group, a vinyl group, a $C_{3-8}$ linear, branched or cyclic hydrocarbon group, or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 0 or 1, to obtain a solution containing the precious metal ions, and subjecting the solution to a reduction treatment to obtain a precious metal.

2. A method for recovering a precious metal, which comprises bringing an adsorbent in which precious metal ions are adsorbed, into contact with a desorbent containing a sulfur-containing amino acid derivative represented by the following formula (I):

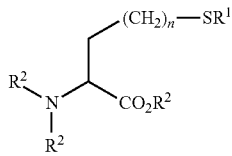

(I)

wherein $R^1$ is a methyl group, an ethyl group, a vinyl group, a $C_{3-8}$ linear, branched or cyclic hydrocarbon group, or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 0 or 1, to obtain a solution containing the precious metal ions, and subjecting the solution to a reduction treatment to obtain a precious metal.

3. The method for recovering a precious metal according to claim 1, wherein the precious metal ions are palladium ions, and the precious metal is palladium.

4. The method for recovering a precious metal according to claim 1, wherein the sulfur-containing amino acid derivative is a compound of the formula (I) wherein $R^1$ is a methyl group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 1.

5. The method for recovering a precious metal according to claim 1, wherein the sulfur-containing amino acid derivative is methionine.

6. The method for recovering a precious metal according to claim 1, wherein the extracting agent or adsorbent contains an amide-containing sulfide compound represented by the formula (II):

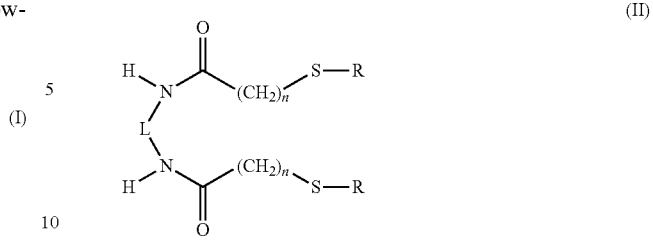

(II)

wherein R's are each independently a methyl group, an ethyl group, a $C_{3-18}$ chain hydrocarbon group, a $C_{3-10}$ alicyclic hydrocarbon group or a $C_{6-14}$ aromatic hydrocarbon group, n's are each independently an integer of from 1 to 4, and L is a methylene group, an ethylene group, a $C_{3-8}$ linear, branched or cyclic alkylene group, or a $C_{6-14}$ arylene group.

7. The method for recovering a precious metal according to claim 6, wherein the amide-containing sulfide compound is a compound of the formula (II) wherein R is n-octyl, and n is 1.

8. The method for recovering a precious metal according to claim 1, wherein the adsorbent is fixed on a carrier.

9. The method for recovering a precious metal according to claim 8, wherein the carrier is alumina or silica gel.

10. The method for recovering a precious metal according to claim 1, wherein the reduction treatment is electrolytic reduction by electrolysis.

11. A back-extracting agent or desorbent, which contains a sulfur-containing amino acid derivative represented by the following formula (I):

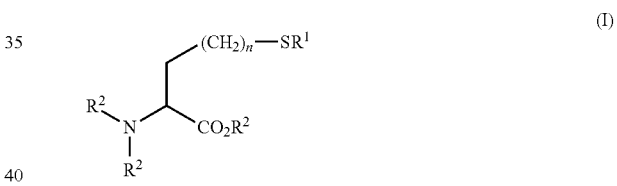

(I)

wherein $R^1$ is a methyl group, an ethyl group, a vinyl group, a $C_{3-8}$ linear, branched or cyclic hydrocarbon group, or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 0 or 1.

12. A desorbent, which contains a sulfur-containing amino acid derivative represented by the following formula (I):

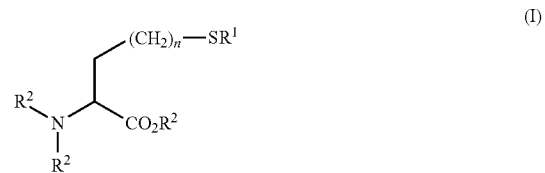

(I)

wherein $R^1$ is a methyl group, an ethyl group, a vinyl group, a $C_{3-8}$ linear, branched or cyclic hydrocarbon group, or a $C_{6-14}$ aromatic hydrocarbon group, $R^2$'s are each independently a hydrogen atom, a methyl group, an ethyl group, a vinyl group, a $C_{3-8}$ linear, branched or cyclic hydrocarbon group or a $C_{6-14}$ aromatic hydrocarbon group, and n is 0 or 1.

13. An extracting agent or adsorbent containing the amide-containing sulfide compound represented by the formula (II):

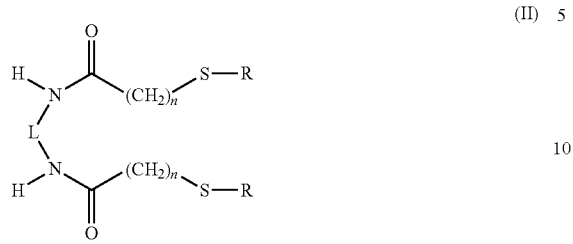

wherein R's are each independently a methyl group, an ethyl group, a $C_{3-18}$ chain hydrocarbon group, a $C_{3-10}$ alicyclic hydrocarbon group or a $C_{6-14}$ aromatic hydrocarbon group, n's are each independently an integer of from 1 to 4, and L is a methylene group, an ethylene group, a $C_{3-8}$ linear, branched or cyclic alkylene group, or a $C_{6-14}$ arylene group.

14. The adsorbent according to claim 13, wherein the amide-containing sulfide compound is fixed on a carrier.

15. The adsorbent according to claim 14, wherein the carrier is alumina or silica gel.

* * * * *